United States Patent
Maddison et al.

(10) Patent No.: US 11,232,354 B2
(45) Date of Patent: Jan. 25, 2022

(54) HISTOPATHOLOGICAL IMAGE ANALYSIS

(71) Applicant: ROOM4 GROUP LIMITED, Crowborough (GB)

(72) Inventors: John Robert Maddison, Crowborough (GB); Havard Danielsen, Oslo (NO)

(73) Assignee: ROOM4 GROUP LIMITED, Crowborough (GB)

( * ) Notice: Subject to any disclaimer, the term of this patent is extended or adjusted under 35 U.S.C. 154(b) by 83 days.

(21) Appl. No.: 16/650,150

(22) PCT Filed: Sep. 7, 2018

(86) PCT No.: PCT/EP2018/074155
§ 371 (c)(1),
(2) Date: Mar. 24, 2020

(87) PCT Pub. No.: WO2019/068415
PCT Pub. Date: Apr. 11, 2019

(65) Prior Publication Data
US 2020/0226462 A1 Jul. 16, 2020

(30) Foreign Application Priority Data
Oct. 2, 2017 (GB) ..................... 1716060

(51) Int. Cl.
*G06K 9/62* (2006.01)
*G06N 3/08* (2006.01)
(Continued)

(52) U.S. Cl.
CPC ............... *G06N 3/08* (2013.01); *G01N 33/53* (2013.01); *G06K 9/0014* (2013.01);
(Continued)

(58) Field of Classification Search
CPC ................ B25B 27/0021; G01N 33/53; G06K 9/00134; G06K 9/0014; G06K 9/32;
(Continued)

(56) References Cited

U.S. PATENT DOCUMENTS

2012/0140999 A1* 6/2012 Kishima ............ G06K 9/00134
382/128
2013/0071002 A1 3/2013 Otsuka
(Continued)

FOREIGN PATENT DOCUMENTS

CN 108 319 815 7/2018
WO 2015/040457 3/2015
(Continued)

OTHER PUBLICATIONS

Ronneberger et al. (O. Ronneberger, P.Fischer. and T. Brox, "U-Net: Convolutional Networks for Biomedical Image Segmentation" Medical Image Computing and Computer-Assisted Intervention (MICCAI), LNCS, vol. 9351, pp. 234-241, Springer, 2015).
(Continued)

*Primary Examiner* — Xin Jia
(74) *Attorney, Agent, or Firm* — Thomas Coester Intellectual Property (57) ABSTRACT

An apparatus and computer-implemented method for training a machine-learning algorithm to perform histopathological analysis is disclosed. The method comprises obtaining (210) a plurality of first microscopic images of first histological specimens that have been stained with a first marker; and obtaining (212), a respective plurality of second microscopic images of second histological specimens that have been stained with a second, different marker. The method further comprises obtaining (220) a respective plurality of mask images generated for the second microscopic images, each mask image identifying a histological feature of inter-
(Continued)

est highlighted in the respective second microscopic image by the second marker. The method comprises training (240) the machine-learning algorithm to predict, from a first microscopic image, a histological feature of interest that would be highlighted in the same specimen by the second marker. Also disclosed is an apparatus and computer-implemented method for histopathological analysis using the trained machine-learning algorithm.

20 Claims, 8 Drawing Sheets

(51) Int. Cl.
    *G06N 20/00*     (2019.01)
    *G01N 33/53*     (2006.01)
    *G06K 9/00*     (2006.01)
    *G06K 9/32*     (2006.01)
    *G06K 9/46*     (2006.01)
    *G06T 7/00*     (2017.01)

(52) U.S. Cl.
    CPC ........... *G06K 9/00134* (2013.01); *G06K 9/32* (2013.01); *G06K 9/4671* (2013.01); *G06N 20/00* (2019.01); *G06T 7/0014* (2013.01); *G06T 2207/10056* (2013.01); *G06T 2207/20021* (2013.01); *G06T 2207/20081* (2013.01); *G06T 2207/20084* (2013.01)

(58) Field of Classification Search
    CPC ........ G06K 9/4671; G06N 20/00; G06N 3/08; G06T 2207/10056; G06T 2207/10064; G06T 2207/20021; G06T 2207/20081; G06T 2207/20084; G06T 2207/30024; G06T 7/0012; G06T 7/0014; Y10T 29/5363

See application file for complete search history.

(56) References Cited

U.S. PATENT DOCUMENTS

| | | |
|---|---|---|
| 2014/0270457 A1 | 9/2014 | Bhargava |
| 2014/0314301 A1* | 10/2014 | Azar ..................... G06T 7/0012 382/133 |
| 2015/0269314 A1* | 9/2015 | Kopriva ................. G16B 45/00 435/40.52 |
| 2015/0279032 A1* | 10/2015 | Hall ........................ G06K 9/00 382/128 |
| 2017/0200067 A1 | 7/2017 | Zhou |
| 2018/0239951 A1* | 8/2018 | El-Zehiry .......... G06K 9/00127 |

FOREIGN PATENT DOCUMENTS

| | | |
|---|---|---|
| WO | 2015/195609 | 12/2015 |
| WO | 2016/146469 | 9/2016 |

OTHER PUBLICATIONS

David Mayerich et al. "Stain-less staining for computed histopathology", Technology (Sillgap World Sci). Mar. 2015; 3(1): 27-31.
Noviello: Patents Act 1977: Search Report under Section 17 dated Mar. 18, 2018.

* cited by examiner

HISTOPATHOLOGICAL IMAGE ANALYSIS

FIELD OF THE INVENTION

This invention relates to analysis of histological images. It relates in particular to using a machine-learning algorithm to perform such analysis and also to training the machine-learning algorithm to perform the analysis.

BACKGROUND OF THE INVENTION

As used herein, a "histological image" refers to an image showing the microscopic structure of organic tissue. A "histological feature of interest" means a feature of this microscopic structure. The feature may be of interest for diagnostic or therapeutic purposes, or for scientific research, for instance. One example of a histological feature of interest is stroma—the connective and supportive framework of a tissue. Identification of stroma in biopsy specimens may be useful for cancer diagnosis and determining prognosis. Another example of a histological feature of interest is chromatin. In general, methods allowing the characterisation of cell nuclei have drug discovery, clinical and other medical applications Conventionally, histological features of interest are identified in histological images by histopathologists—specialist medical experts trained in the interpretation of these images.

At the microscopic scale, many of the interesting features of cells are not naturally visible, because they are transparent and colourless. To reveal these features, specimens are commonly stained with a marker before being imaged under a microscope. The marker includes one or more colorants (dyes or pigments) that are designed to bind specifically to particular components of the cell structure, thus revealing the histological feature of interest.

The marker is selected according to the feature that is desired to be examined. Thus, to examine different features, different markers may be needed. The most commonly used staining system is called H&E (Haemotoxylin and Eosin). H&E contains the two dyes haemotoxylin and eosin. Eosin is an acidic dye—it is negatively charged. It stains basic (or acidophilic) structures red or pink. Haematoxylin can be considered as a basic dye. It is used to stain acidic (or basophilic) structures a purplish blue.

DNA (heterochromatin and the nucleolus) in the nucleus, and RNA in ribosomes and in the rough endoplasmic reticulum are both acidic, and so haemotoxylin binds to them and stains them purple. Some extracellular materials (i.e. carbohydrates in cartilage) are also basophilic. Most proteins in the cytoplasm are basic, and so eosin binds to these proteins and stains them pink. This includes cytoplasmic filaments in muscle cells, intracellular membranes, and extracellular fibres.

Unfortunately, many features of interest are still difficult or impossible for a histopathologist to see or accurately quantify with H&E staining. For this reason, other marker systems have been developed.

A particularly important class of markers relates to the field of immunohistochemistry (IHC). IHC allows antigens (for example, proteins) in the cells of a tissue section to be selectively imaged by binding antibodies specifically to the antigens of interest in biological tissues. However, IHC is not without drawbacks. IHC techniques may be expensive, time-consuming, and/or difficult to implement.

SUMMARY OF THE INVENTION

The invention is defined by the claims. According to a first aspect of the invention, there is provided a computer-implemented method of training a machine-learning algorithm to perform histopathological image analysis, the method comprising:

obtaining, by the computer, a plurality of first microscopic images of first histological specimens that have been stained with a first marker;

obtaining, by the computer, a respective plurality of second microscopic images of second histological specimens that have been stained with a second marker, different from the first marker, each one of the second histological specimens corresponding to a respective one of the first histological specimens;

obtaining, by the computer, a respective plurality of mask images generated for the second microscopic images, each mask image identifying a histological feature of interest highlighted in the respective second microscopic image by the second marker;

for each first microscopic image and the respective second microscopic image and mask image:
  obtaining, by the computer, a transformation that maps between the first microscopic image and the second microscopic image, and
  aligning, by the computer, the first microscopic image and the mask image, using the transformation; and
training, by the computer, the machine-learning algorithm with the plurality of aligned first microscopic images and mask images, thereby training the machine-learning algorithm to predict, from another first microscopic image of another histological specimen stained with the first marker, a histological feature of interest that would be highlighted in that specimen by the second marker.

Surprisingly, the inventors have found that it is possible to obtain, by using only a first marker, results that would usually require a second marker. Whereas the histological feature of interest may only be visible to a human user when specimens are stained with the second marker, a machine-learning algorithm may be trained to identify characteristics corresponding to the same histological feature of interest, in images of specimens stained with the first marker. Fundamentally, the visual information needed to identify the feature may be present in the image of the specimen stained with the first marker. But the human visual system may not be well-suited or not sensitive enough to detect it. Even if it is possible for a human user to see the feature of interest in specimens stained with the first marker, the human user may find it difficult, or not feasible in practice, to identify exhaustively all instances of the feature in a large collection of such images. Manually annotating many very large images to highlight the feature of interest would be extremely time-consuming and laborious. Furthermore, with manual annotation, it is very difficult to achieve consistency (either among different images annotated by the same user, or between users). Therefore, when relying on human review of such samples it is very difficult to obtain any repeatable objective measures.

The trained machine-learning algorithm can therefore perform surprisingly better than a human expert at this task. Embodiments of the present invention can allow different types of analysis to be simulated on a single specimen, stained with a single marker. Previously, this would have required different specimens, stained with different markers. Furthermore, embodiments can allow analysis to be carried out with a first marker that is quicker, easier, or cheaper to use than a second marker, and yet to obtain simulated results that are comparable with those that would actually be obtained using the second marker.

The method can train the machine-learning algorithm to predict from another first microscopic image of another histological specimen, stained with the first marker, the mask image that would be generated for a second microscopic image of that histological specimen if it had been stained with the second marker.

The first microscopic images may provide the training inputs for training the neural network. The mask images may provide the desired outputs associated with those training inputs.

Each microscopic image is preferably a grayscale or colour image consisting of one, two or three colour channels. Most preferably, it is a colour image consisting of three colour channels. Thus, it provides three samples for each pixel. The samples are coordinates in a three-dimensional colour space. Suitable 3-D colour spaces include but are not limited to RGB, HSV, YCbCr, and YUV.

The second histological specimens may "correspond" to the first histological specimens in a variety of ways. In some embodiments, the first specimen and the second specimen may be the same specimen that has been de-stained and then re-stained with a different marker. In other embodiments, the first specimen and the second specimen may be adjacent sections (slices) of biological tissue. Using adjacent sections can avoid the need to de-stain and re-stain (which may be difficult or impossible in some cases). However, using the same section can mean that the transformation between the first image and the second image is less complex, more accurate, and/or easier to determine.

Each mask image may comprise a binary image, or a multi-level image. A multi-level image may provide a scalar indication of the histological feature of interest—thus providing a heat map highlighting areas where a strength or probability of occurrence of the histological feature of interest is high, for example.

The transformation that maps between the first microscopic image and the second microscopic image is preferably a geometric transformation, such as an affine transformation.

The method may further comprise obtaining, by the computer, a region of interest in each of the first microscopic images, the method comprising training the machine-learning algorithm with said regions of interest and excluding from the training any regions other than said regions of interest.

In some embodiments, the region of interest may be generated by the computer—for example, using an image segmentation algorithm. In some embodiments, the region of interest may be input by a user, such as a histopathologist. In some embodiments, the region of interest may be generated semi-automatically, with some user input combined with some image segmentation by the computer.

The method may further comprise dividing, by the computer, each of the aligned first microscopic images and mask images into first tiles and mask tiles, respectively, the method comprising training the machine-learning algorithm with said first tiles and said mask tiles.

Dividing the training images (and mask images) into tiles both increases the amount of training data available and can be used to control the size and/or complexity of the machine-learning algorithm, by controlling the amount of input information to be analysed. Essentially, the machine-learning algorithm is being trained to classify each pixel of a tile as exhibiting the histological feature of interest, or not, based on the content of that pixel and the other pixels of tile.

Obtaining the respective plurality of mask images optionally comprises generating, by the computer, each mask image from the respective second microscopic image.

For example, the computer may generate the mask image by automatically segmenting the second microscopic image into pixels having the histological feature of interest and pixels not having the histological feature of interest.

Such automatic segmentation may comprise applying one or more thresholds to one or more colour channels of the image. Alternatively, or in addition, it may comprise operations such as morphological processing, and/or eliminating regions that are smaller than a predetermined size threshold.

In some embodiments, the mask image may be generated manually or semi-automatically.

One or both of the following steps is preferably performed first at a coarse scale or resolution and subsequently performed at a fine scale or resolution: (a) obtaining the transformation; and (b) aligning the first microscopic image and the mask image.

Obtaining the transformation may comprise obtaining a first, large scale transformation that applies to the whole image. It may further comprise obtaining one or more second, small scale transformations that apply to individual tiles of the image. Such a multi-scale or multiresolution approach can allow better and/or more efficient alignment.

Obtaining the transformation optionally comprises extracting features of interest from the first microscopic image and the second microscopic image and establishing a mapping between the features of interest.

One particularly suitable technique of this kind is the Scale-Invariant Feature Transform (SIFT).

The first marker may comprise haemotoxylin and eosin.

Haemotoxylin and Eosin (H&E) dye is relatively cheap and widely used in the art to stain histological specimens. It is particularly advantageous to be able to perform, using images of H&E-stained specimens, histopathological analysis that could previously only be performed with other, more expensive, or more time consuming marking techniques. Such analysis can be performed according to embodiments of the present invention.

The second marker may comprise an immunohistochemical marker.

The immunohistochemical markers may comprise an antibody marker. Some immunohistochemical markers of particular interest are those listed in the detailed description below, including: Vimentin; PD-L1; and Ki67.

In some embodiments, the first marker may comprise a first immunohistochemical marker and the second marker may comprise a second immunohistochemical marker. In this way, features typically expressed better by one IHC marker may be identified using a different IHC marker. Likewise, this approach can also enable analysis to be conducted using a single IHC marker, which would previously have required to IHC markers.

The second marker may comprise a fluorescence marker.

The machine-learning algorithm preferably comprises a neural network.

One particularly suitable neural network structure for use in the present method is a U-net convolution network.

The method may further comprise training the machine-learning algorithm to predict, from a first microscopic image of a histological specimen stained with the first marker, a further histological feature of interest that would be highlighted in that specimen by a third marker, different from the first and second markers.

This can allow the machine-learning algorithm to extract even more useful information from first microscopic images of specimens stained with the first marker. For example, the machine-learning algorithm could be trained to identify a first histological feature of interest and a second histological feature of interest. This would allow automated analysis of the regions of overlap between the two features of interest, for example.

The training can comprise repeating the same sequence of steps that was used to train the algorithm to recognise the first histological feature of interest. The training data would comprise third microscopic images of histological specimens stained with the third marker and further mask images for those third images, respectively.

According to a second aspect of the invention, there is provided a computer-implemented method for histopathological image analysis, using a machine-learning algorithm trained according to a method as summarised above, the analysis method comprising:

obtaining, by the computer, a first microscopic image of a histological specimen that has been stained with the first marker;

providing, by the computer, the trained machine-learning algorithm;

processing, by the computer, the first microscopic image using the machine-learning algorithm, to analyse the first microscopic image and generate a mask image, whereby the mask image identifies a histological feature of interest detectable using the second marker.

The mask image generated by the machine-learning algorithm may be a binary mask, which indicates the presence and absence of the histological feature of interest in a purely binary fashion, or it may be a multi-level mask, which indicates the presence and absence of the histological feature of interest in a scalar or probabilistic fashion. A binary mask image may be generated from a multi-level mask image by thresholding.

The machine-learning algorithm has optionally been trained to predict, from the first microscopic image, a further histological feature of interest detectable using a third marker, wherein, in processing the first microscopic image, the computer generates a further mask image identifying the further histological feature of interest.

The machine-learning algorithm could be trained to predict one histological feature of interest detectable with one IHC marker, and to predict another histological feature of interest detectable with another IHC marker. These results may then be combined.

For example, it is possible to use the CK8 marker to accurately select epithelial areas and then to use the Ki67 marker to highlight proliferating cells within the epithelial areas. This analysis may be conducted using H&E staining of a single specimen, according to one embodiment of the invention.

The method may further comprise conducting, by the computer, automated analysis of the mask image and/or the further mask image.

In this way, the mask (and/or further mask) can be used in subsequent analysis. For example, object-based metrics such as texture, intensity, area, and other morphological characteristics may be calculated. Alternatively, or in addition, field-based metrics such as total area covered or other metrics derived from the structure of the specimen as a whole may be calculated.

The mask and further mask may be used separately or combined—for example, the automated analysis may comprise calculating an area of overlap (intersection) between the mask and the further mask.

Embodiments of the invention can thus subsequently allow for the quantification of the result as per existing IHC analysis for both object and frame or slide based analysis.

Also disclosed is a computer program product comprising a non-transitory computer-readable medium having embodied thereon a computer program comprising computer program code configured to control a computer to execute all the steps of a method as summarised above when said computer program is run on the computer.

Also disclosed is a histopathological image analysis apparatus comprising:
a computer-readable storage medium;
a memory;
one or more interfaces; and
a processor configured to perform a method as summarised above.

BRIEF DESCRIPTION OF THE DRAWINGS

The invention will now be described by way of example with reference to the accompanying drawings, in which.

DETAILED DESCRIPTION

Figure 1:
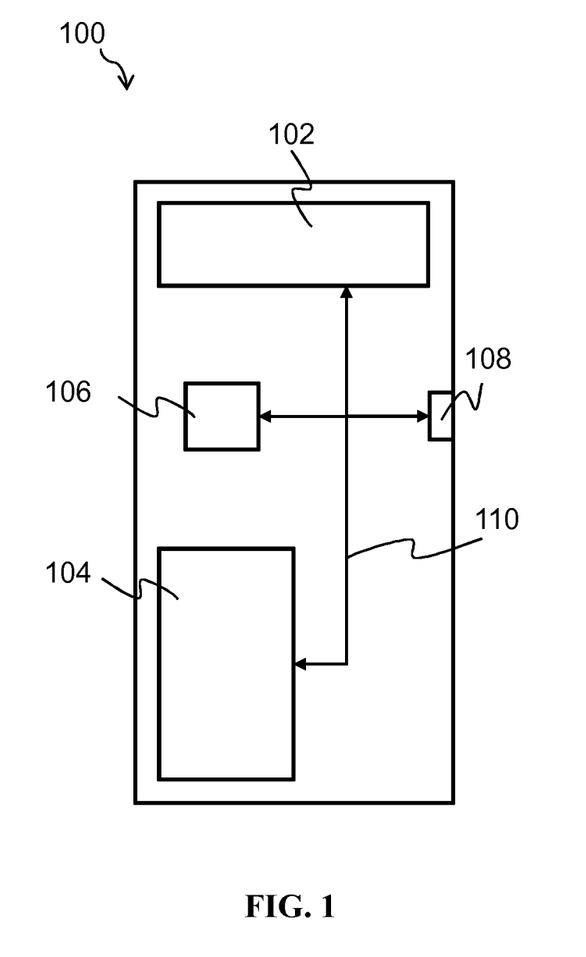
FIG. 1 is a block diagram schematically illustrating an exemplary computer system upon which embodiments of the present invention may run.

FIG. 1 of the accompanying drawings schematically illustrates an exemplary computer system 100 upon which embodiments of the present invention may run. The exemplary computer system 100 comprises a computer-readable storage medium 102, a memory 104, a processor 106 and one or more interfaces 108, which are all linked together over one or more communication busses 110. The exemplary computer system 100 may take the form of a conventional computer system, such as, for example, a desktop computer, a personal computer, a laptop, a tablet, a smart phone, a smart watch, a virtual reality headset, a server, a mainframe computer, and so on. In some embodiments, it may be embedded in a microscopy apparatus, such as a virtual slide microscope capable of whole slide imaging.

The computer-readable storage medium 102 and/or the memory 104 may store one or more computer programs (or software or code) and/or data. The computer programs stored in the computer-readable storage medium 102 may include an operating system for the processor 106 to execute in order for the computer system 100 to function. The computer programs stored in the computer-readable storage medium 102 and/or the memory 104 may include computer programs according to embodiments of the invention or computer programs that, when executed by the processor 106, cause the processor 106 to carry out a method according to an embodiment of the invention The processor 106 may be any data processing unit suitable for executing one or more computer readable program instructions, such as those belonging to computer programs stored in the computer-readable storage medium 102 and/or the memory 104. As part of the execution of one or more computer-readable program instructions, the processor 106 may store data to and/or read data from the computer-readable storage medium 102 and/or the memory 104. The processor 106 may comprise a single data processing unit or multiple data processing units operating in parallel or in cooperation with each other. In a particularly preferred embodiment, the processor 106 may comprise one or more Graphics Processing Units (GPUs). GPUs are well suited to the kinds of calculations involved in training and using machine-learning algorithms such as those disclosed herein. The processor 106 may, as part of the execution of one or more computer readable program instructions, store data to and/or read data from the computer-readable storage medium 102 and/or the memory 104.

The one or more interfaces 108 may comprise a network interface enabling the computer system 100 to communicate with other computer systems across a network. The network may be any kind of network suitable for transmitting or communicating data from one computer system to another. For example, the network could comprise one or more of a local area network, a wide area network, a metropolitan area network, the internet, a wireless communications network, and so on. The computer system 100 may communicate with other computer systems over the network via any suitable communication mechanism/protocol. The processor 106 may communicate with the network interface via the one or more communication busses 110 to cause the network interface to send data and/or commands to another computer system over the network. Similarly, the one or more communication busses 110 enable the processor 106 to operate on data and/or commands received by the computer system 100 via the network interface from other computer systems over the network.

The interface 108 may alternatively or additionally comprise a user input interface and/or a user output interface. The user input interface may be arranged to receive input from a user, or operator, of the system 100. The user may provide this input via one or more user input devices (not shown), such as a mouse (or other pointing device, track-ball or keyboard. The user output interface may be arranged to provide a graphical/visual output to a user or operator of the system 100 on a display (or monitor or screen) (not shown). The processor 106 may instruct the user output interface to form an image/video signal which causes the display to show a desired graphical output. The display may be touch-sensitive enabling the user to provide an input by touching or pressing the display.

According to embodiments of the invention, the interface 108 may alternatively or additionally comprise an interface to a digital microscope or other microscopy system. For example, the interface 108 may comprise an interface to a virtual microscopy apparatus capable of Whole Slide Imaging (WSI). In WSI, a virtual slide is generated by high-resolution scanning of a glass slide by a slide scanner. The scanning is typically done piecewise and the resulting images are stitched together to form one very large image at the highest magnification of which the scanner is capable. These images may have dimensions of the order of 100,000×200,000 pixels—in other words, they may contain several billion pixels. According to some embodiments, the computer system 100 may control the microscopy apparatus through the interface 108 to scan slides containing specimens. The computer system 100 may thus obtain microscopic images of histological specimens from the microscopy apparatus, received through the interface 108.

It will be appreciated that the architecture of the computer system 100 illustrated in FIG. 1 and described above is merely exemplary and that systems having different architectures using alternative components or using more components (or fewer) may be used instead.

Figure 2:
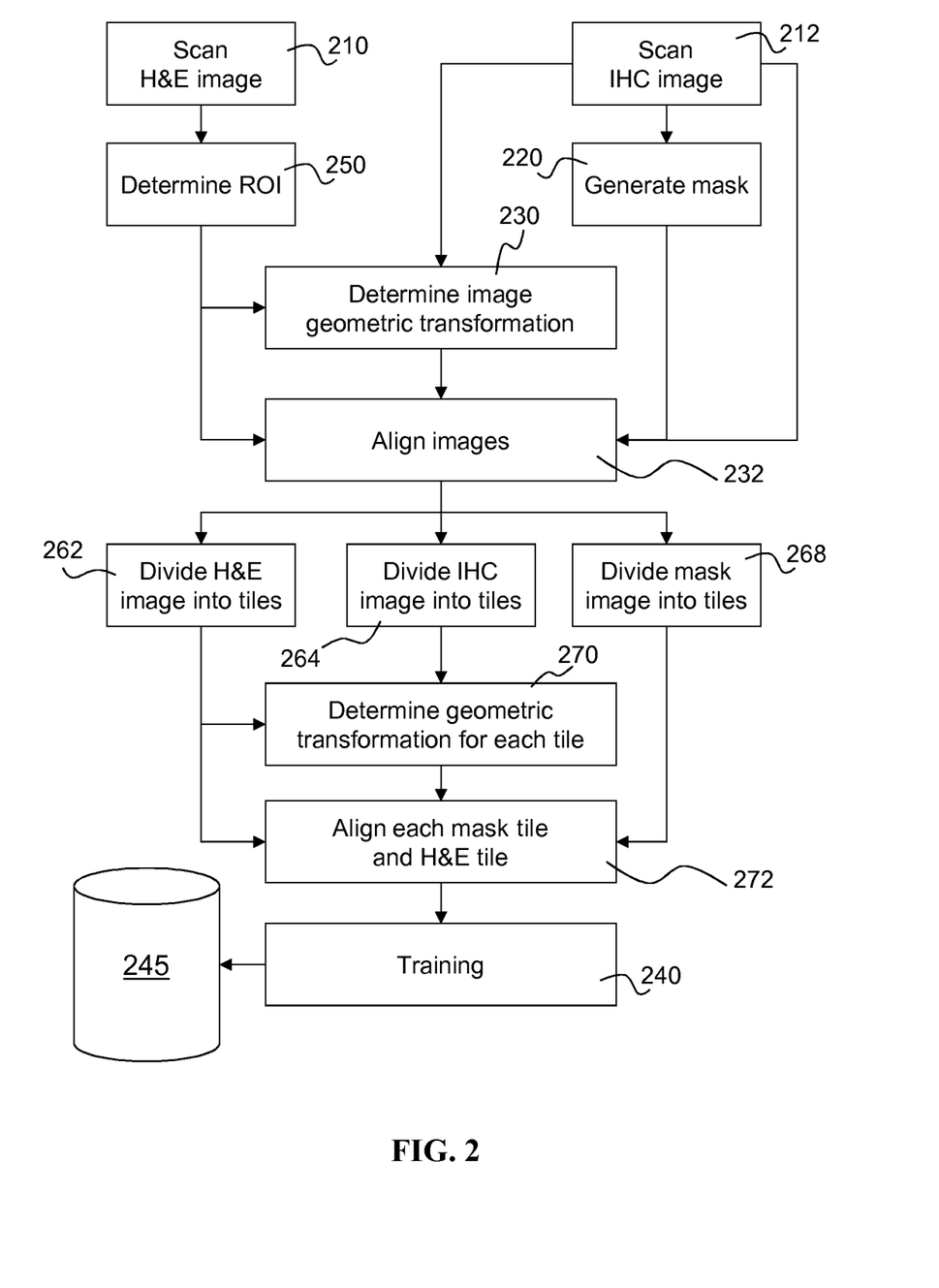
FIG. 2 is a flowchart of a method of training a machine-learning algorithm, according to an embodiment of a first aspect of the invention.

FIG. 2 is a flowchart showing a method of training a machine-learning algorithm to perform histopathological image analysis, according to an embodiment of a first aspect of the invention. The method uses a set of training images to train the algorithm to detect a histological feature of interest. In particular, it trains the algorithm to detect, in images stained with one marker, a histological feature that is usually detected (and typically is more easily detectable by a human expert) in images stained with another, different marker.

In step 210, the computer 100 obtains a plurality of first colour microscopic images of first histological specimens that have been stained with a first marker. To do this, the computer controls a Virtual Microscope (VM) to scan slides containing the specimens. One suitable group of virtual microscopes is sold by Hamamatsu Photonics of Japan, under the product name "NanoZoomer". The virtual microscope comprises microscope optical components, a stage for mounting the specimen to be examined, a Charge-Coupled Device (CCD) array or other electronic imaging device for receiving the image of the specimen, a computer for processing the image and a Visual Display Unit (VDU) for displaying the image and other data. A prepared slide containing a slice of biological tissue is scanned by the virtual microscope to produce a respective first colour microscopic image. For each point (pixel) on on the image, the CCD array includes red, green, and blue wavelength detectors, providing respective red, green, and blue signals. Thus, the virtual microscope produces a colour image consisting of three colour channels. In the present example, the maximum magnification provided by the virtual microscope corresponds to approximately a 40x objective optical microscope lens when used on a standard bright field microscope.

Figure 4:
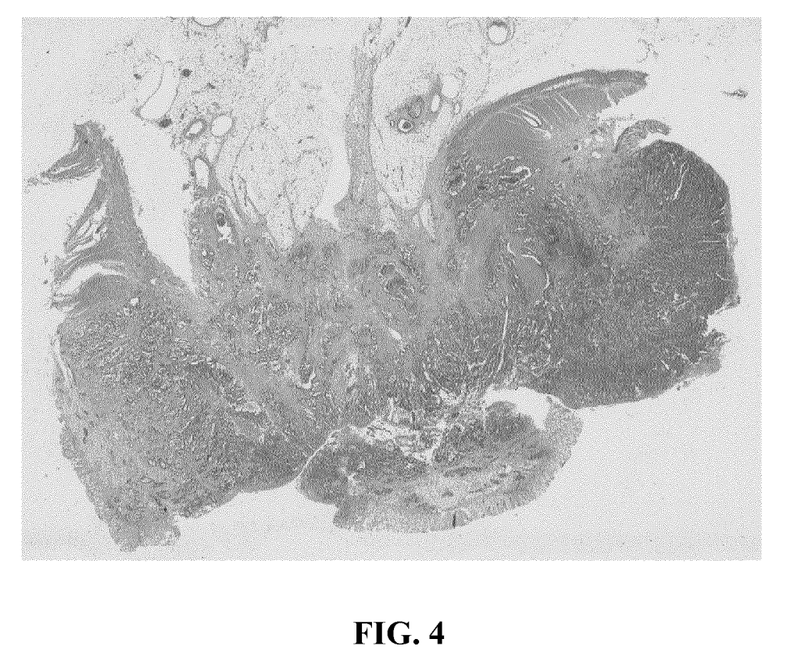
FIG. 4 is an exemplary first microscopic image showing a biological tissue specimen stained with H&E stain.

In the present embodiment, the first marker comprises H&E stain. FIG. 4 is an example of a first colour microscopic image. The image shows a first biological tissue specimen that has been stained with H&E stain. The stain highlights the structure of the cellular material in the biological specimen.

In step 212, the computer 100 obtains a plurality of second colour microscopic images of second histological specimens that have been stained with a second, different marker. Each one of the second histological specimens corresponds to a respective one of the first histological specimens. Thus, each one of the second colour microscopic images corresponds to a respective one of the first colour microscopic images.

Correspondence between the specimens may be achieved in a variety of ways. In the present embodiment, each first specimen and the respective second specimen are adjacent slices (serial sections) from the same piece of tissue. Thus, although there may be slight differences, there is a strong correlation between the structures shown in both images. As an alternative, the same specimen may be used as both a first specimen and a second specimen. However, this would typically require de-staining the specimen and re-staining it with another marker. This may be difficult or impossible in some circumstances and/or for some combinations of first and second markers.

Figure 5:
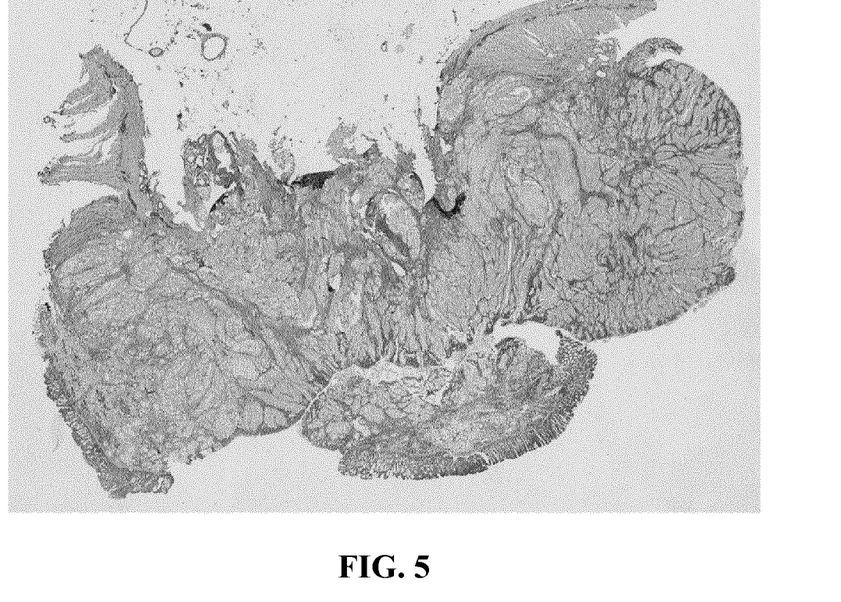
FIG. 5 is an exemplary second microscopic image, corresponding to the first microscopic image, showing a biological tissue specimen stained with the IHC stain Vimentin.

In the present embodiment, the second marker comprises Vimentin, an IHC stain. This stains stroma a dark brown colour. FIG. 5 is an example of a second colour microscopic image showing a second biological tissue specimen that has been stained with Vimentin. The second tissue specimen corresponds to the first tissue specimen of FIG. 4, by virtue of being an adjacent micro-tome slice, as explained above. As can be seen, the overall structure of the two slices is very similar; however, the use of different markers highlights different aspects of this structure.

Figure 6:
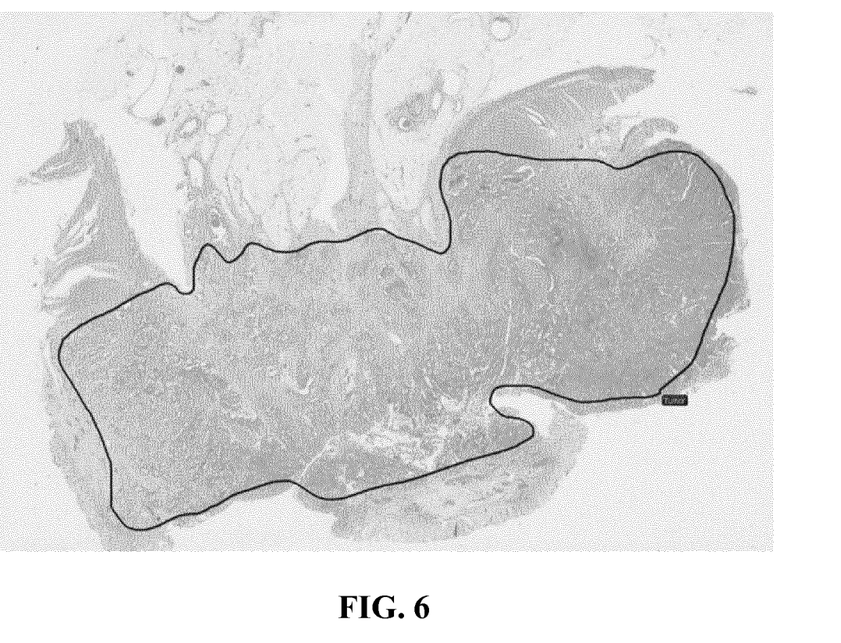
FIG. 6 shows the first microscopic image of FIG. 4 hand-annotated with a region of interest.

Optionally, in step 250, the analysis may be confined to a specific portion of the image, by determining a Region of Interest (ROI). In general, the ROI may be selected manually, automatically, or semi-automatically. In the present embodiment, the computer 100 determines the region of interest by requesting user-input to define it. The user can do this by annotating the first colour image with a closed contour such as a bounding box. Preferably however, the user can draw a free-hand closed contour to select the ROI. An example of this is shown in FIG. 6, where a pathologist has manually identified a region of interest on the first colour image of FIG. 4. In this particular instance, the ROI corresponds to a tumour identified by the pathologist. The closed contour selected by the pathologist and input to the computer is shown as a black line.

Figure 7:
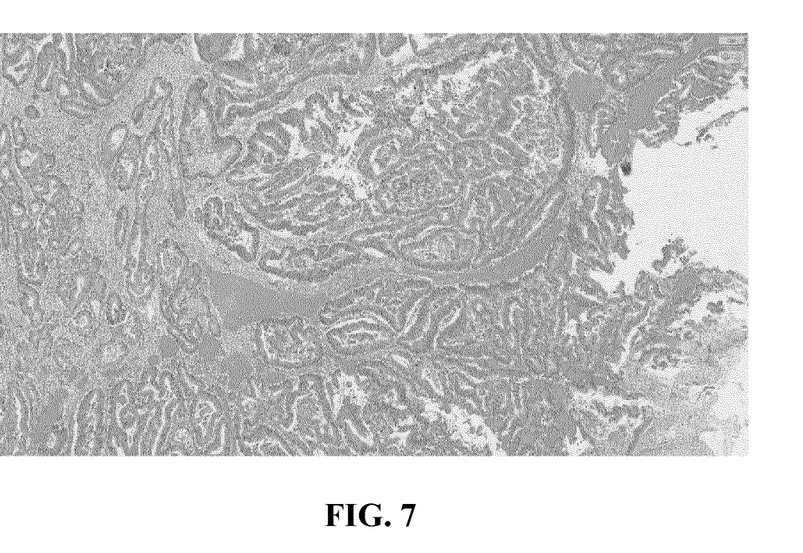
FIG. 7 shows a zoomed in detail of part of the first microscopic image of FIG. 4.
Figure 8:
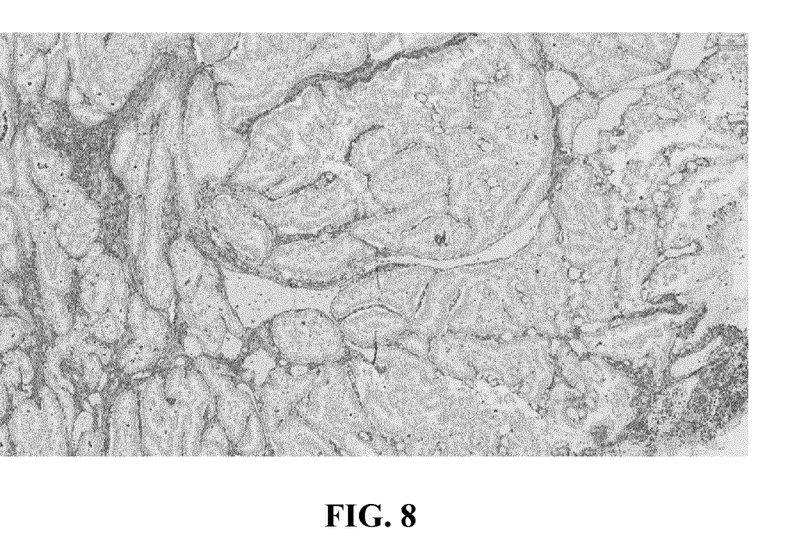
FIG. 8 shows a zoomed in detail of a corresponding part of the second microscopic image of FIG. 5.

FIG. 7 shows a zoomed-in detail of one part of the ROI in the first colour microscopic image of FIG. 4. Meanwhile, FIG. 8 shows a corresponding zoomed-in detail from the second colour microscopic image of FIG. 5.

The aim of the method is to train the machine-learning algorithm to emulate how the histological feature of interest is extracted from the second colour microscopic image. In order to do this, a training output is required—in other words, the machine-learning algorithm needs examples of the desired analysis results for the second colour microscopic images. These desired analysis results are mask images highlighting the histological feature of interest in the respective second colour microscopic images.

The mask images for training may be obtained in a variety of different ways. In some cases, a manually generated "ground truth" may be available—for example, if the second colour images have already been manually annotated by a pathologist to identify the feature of interest. However, in many cases, it will be too time-consuming to manually annotate a sufficient number of images for training the machine-learning algorithm. To address this difficulty, the computer 100 can obtain the mask images by automatically generating them from the second colour microscopic images.

In the present embodiment, the computer 100 automatically generates the mask images in step 220. Each second colour microscopic image (showing the Vimentin stained specimen) is converted to the Hue Saturation Value (HSV) colour space and the mask is extracted by applying thresholds in this space. In particular, pixels are included in the mask if they have Hue (H) in the range 0.8 to 0.0 and 0.0 to 0.2 (that is, in the range of ±0.2 about 0.0) and Value (V) less than 0.9. This method will select the dark brown coloured pixels, where the Vimentin stain has highlighted stroma. Small regions and holes in the mask are then eliminated. In particular, a region will be removed, or a hole will be filled in, if its area is less than 200 pixels.

Note that the present example assumes that the mask image is a binary image, denoting the presence or absence of stroma. However, in other embodiments, the mask image may be a multi-level mask. Such a multi-level mask may indicate, for each pixel of the mask, a probability or confidence that the pixel represents stroma.

To prepare the images to train the machine-learning algorithm, they should be aligned. There will always be geometric placement differences when the specimens are placed on their slides. And the use of different markers will highlight or emphasise different aspects of the structure of the tissue. In addition, in the present embodiment, there are physical differences in the specimens, because they are adjacent serial sections rather than the same specimen. For all these reasons, it is necessary to establish a mapping between corresponding structures in each first colour microscopic image and its respective second colour microscopic image.

To do this, the computer 100 in step 230 obtains a geometric transformation that maps between the first colour microscopic image and the second colour microscopic image. In the present embodiment, this is done using the Scale Invariant Feature Transform (SIFT). This technique has been found to work well, but those skilled in the art will appreciate that other techniques for image registration and alignment may also be suitable. These may include other scale invariant transforms, and also other alignment methods such as those described in GB 2434651.

Note that the SIFT is a fully automated method but, in some embodiments, the geometric transformation may be determined semi-automatically and/or based on user input. For example, the pathologist could manually select a number of corresponding structural features in the two images and the computer 100 could calculate the geometric transformation from these manually selected features.

In step 232, the computer 100 applies the geometric transformation that was determined in step 230 to align the images. In the present example, the geometric transformation is an affine transformation. However, as those skilled in the art will appreciate, other types of geometric transformation could be used in place of the affine transformation.

Ultimately, the goal is to align each first colour microscopic image with its respective mask image, since these pairs of images will be used to train the machine-learning algorithm. However, this goal may be achieved in a number of different ways, applying the geometric transformation to one or more of a number of different images. In general, the transformation could be applied to the first colour microscopic image to align it with the mask image, or it could be applied to the mask image to align it with the first colour microscopic image. Another alternative is to apply the transformation to the second colour microscopic image to align it with the first colour microscopic image, before extracting the mask image from the aligned second colour microscopic image. Different approaches may have different benefits, depending on the usage scenario.

Figure 9:
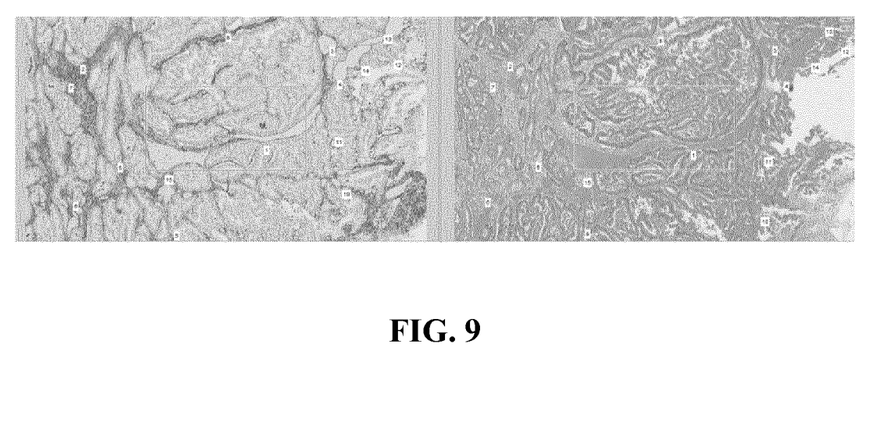
FIG. 9 illustrates one way to determine a geometric transformation that maps between the first microscopic image of FIG. 7 and the second microscopic image of FIG. 8.

FIG. 9 shows the application of the SIFT algorithm to the detailed first and second colour microscopic images of FIGS. 7 and 8. Each white box represents a feature point that has been identified by the SIFT procedure and matched with a counterpart feature point in the other image.

Figure 10:
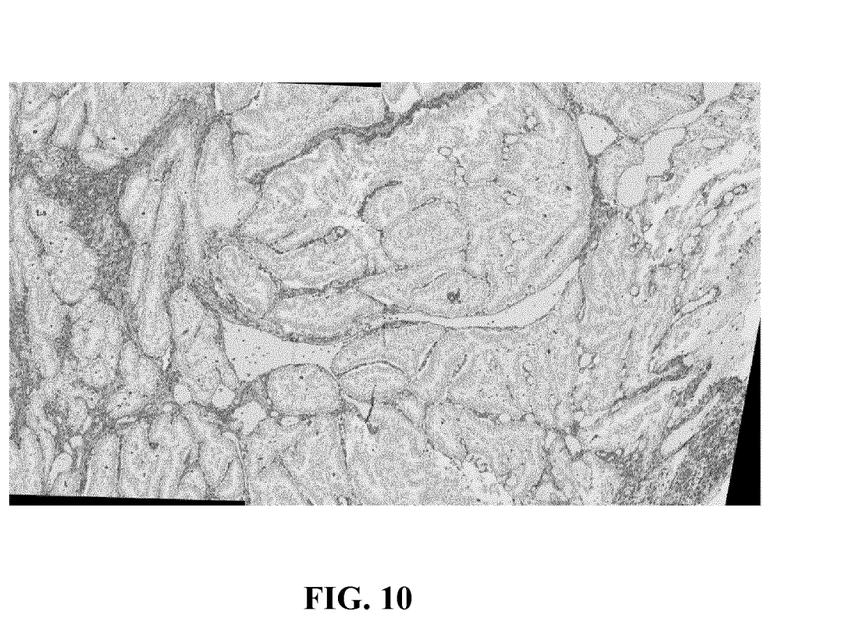
FIG. 10 illustrates the result of applying the geometric transformation to the second microscopic image of FIG. 8.

FIG. 10 shows the result of applying the determined geometric transformation to the second colour microscopic image of FIG. 8.

Figure 11:
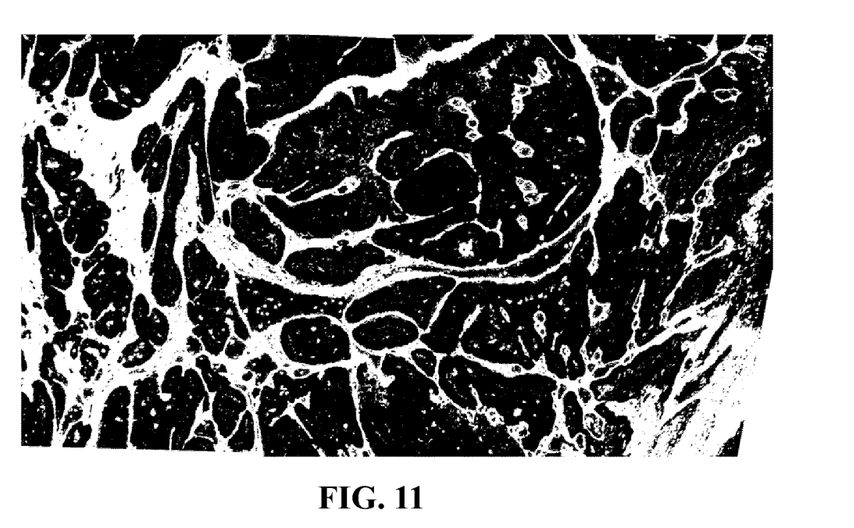
FIG. 11 shows a mask image obtained for the aligned second microscopic image of FIG. 10.

FIG. 11 is an exemplary mask image extracted from the aligned second colour microscopic image of FIG. 10. The white pixels show where stroma has been detected in the second colour microscopic image (by means of the brown staining with the IHC marker, Vimentin). The mask was extracted automatically using the heuristic thresholding method discussed previously above.

Because of the extremely high resolution of the virtual microscope images, and because of local variations in the mapping between the first and second colour microscopic images, it may be advantageous to determine the geometric transformation and align the images using a multiscale or multiresolution approach.

Such an approach is taken in the embodiment illustrated in FIG. 2. In step 230, a geometric transformation is determined at a low resolution and large scale. This geometric transformation is applied on a global basis in step 232. After this alignment, the respective images are divided into smaller tiles to train the machine-learning algorithm. In step 262, the computer 100 divides the first colour microscopic images into tiles; in step 264 the computer 100 divides the second colour microscopic images into tiles; and in step 268, the computer 100 divides the mask images into tiles. The process of determining a geometric transformation and aligning the images is repeated for each tile. In step 270, the computer 100 determines a geometric transformation at a high resolution and small scale, for each tile. In the present example, this is again done using the SIFT. In step 272, the computer 100 applies, to each tile, the respective geometric transformation determined in step 270. Like step 232, in the present embodiment the geometric transformation is an affine transformation.

If has been found that the alignment strategy described above can improve the alignment of the tiles and can allow for local variations in the geometric transformation.

In step 240, the aligned tiles are used to train the machine-learning algorithm. In the present embodiment, the individual tiles are 512×512 pixels in size. The preferred machine-learning algorithm is a neural network. In particular, in the present embodiment, a U-Net convolution network was used. The design and training of such a network is described in greater detail in Ronneberger et al (O. Ronneberger, P. Fischer. and T. Brox, "U-Net: Convolutional Networks for Biomedical Image Segmentation" Medical Image Computing and Computer-Assisted Intervention (MICCAI), LNCS, volume 9351, pages 234-241, Springer, 2015), where binary cross entropy is used in the loss function, (Mean Squared error for example would be more suitable for scalar values of the mask). As those skilled in the art will appreciate from reading the foregoing description, other neural network topologies may also be suitable.

To increase the amount of training data, random horizontal and vertical flipping of the training images was applied. Augmentation was also applied to HSV channels. In particular, additional training images were generated by multiplying the HSV channels of real images by random scaling factors. This can help to improve the generalization ability of the machine-learning algorithm, by discouraging it from specializing on the exact colours found in the (real) training images. In other words, introducing this additional variation into the training dataset can help to improve the robustness of the machine-learning algorithm.

The training results in a set of weights 245 for the neural network. The weights define the operation of the neural network by specifying the relationships between the inputs and outputs. The weights 245 are stored in the computer-readable storage medium 102, for later use in analysing histological images. Whereas a neural network is defined by its weights, other machine-learning algorithms may be defined by other parameters. In that case, those other learned parameters would be stored in the computer-readable storage medium in place of the neural network weights.

Figure 3:
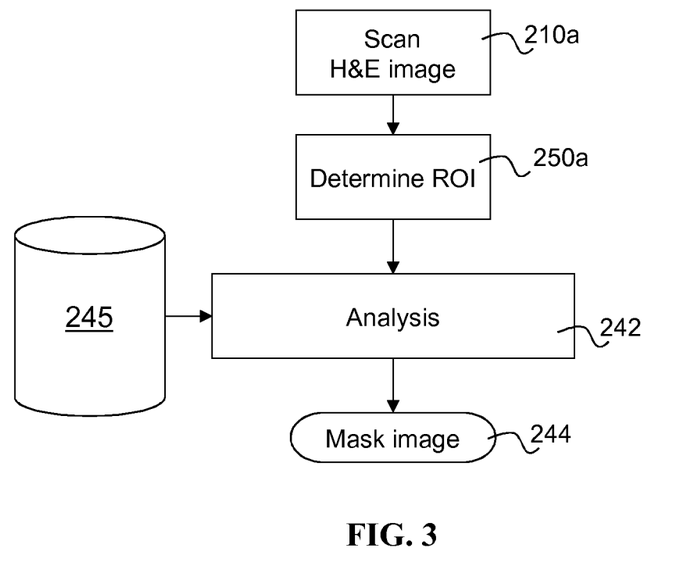
FIG. 3 is a flowchart showing a method for histopathological image analysis, according to an embodiment of a second aspect of the invention.

The trained machine-learning algorithm is now ready for use in analysing histological images. FIG. 3 illustrates a method for histopathological image analysis according to an embodiment of the second aspect of the invention.

In step 210a, the computer 100 obtains a first colour microscopic image of a histological specimen has been stained with the first marker. This step is substantially similar to step 210 of FIG. 2, in that it comprises the computer controlling a virtual microscope to scan an image of a specimen stained with H&E.

In step 250a, the computer 100 obtains a region of interest in the first colour microscopic image. This step is substantially similar to step 250 in the method of FIG. 2, in that the region of interest is manually selected by an expert human user.

In step 242, the computer processes the first colour microscopic image using the machine-learning algorithm to thereby analyse the image and generate a mask image. In the present embodiment, this comprises retrieving the trained neural network weights 245 from the computer readable storage medium 102 and applying the first colour microscopic image to the neural network having those weights. In response, the neural network outputs a mask image 244 identifying the histological feature of interest (in this case, stroma).

Note that, in the method according to the second aspect of the invention, there is no second colour microscopic image of a corresponding sample stained with Vimentin. The machine-learning algorithm is able to estimate or predict, from the first colour microscopic image, which parts of the image correspond to the histological feature of interest (in this case, stroma). It has learned to infer this by being trained with mask images identifying the histological feature of interest in the training images.

Figure 12:
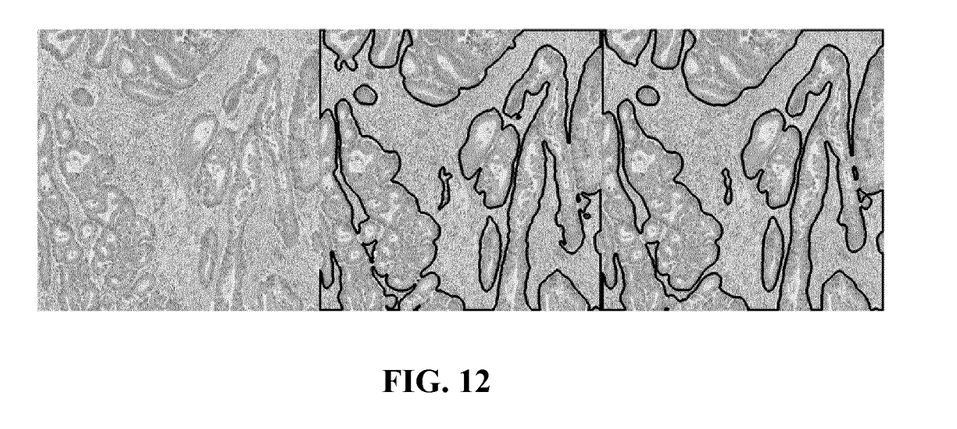
FIG. 12 shows results obtained using an image analysis method according to an embodiment of the second aspect of the invention, using a training image as the input image.

FIG. 12 shows a first example of the results produced by the method of FIG. 3. On the left-hand side is the original first colour microscopic image, showing a specimen stained with H&E. In other words, the left-hand side shows the input image. In the centre, the input image is overlaid with a mask image obtained from a corresponding IHC image (a second colour microscopic image of a corresponding specimen stained with Vimentin). In other words, the central image shows the desired result. The black lines denote the boundaries between the stroma areas and non-stroma areas. The right-hand side shows the actual result of processing using the trained neural network. Again, this is presented as a mask image overlaid on the input image. And again, the black lines denote boundaries between stroma and non-stroma. The similarity between the image in the centre and the image on the right-hand side demonstrates the effectiveness of the method.

In the example of FIG. 12, one of the training images was used as an input image. Although this validates that the neural network has been trained properly, it does not necessarily prove that the neural network is capable of generalising to other, unseen examples.

Figure 13:
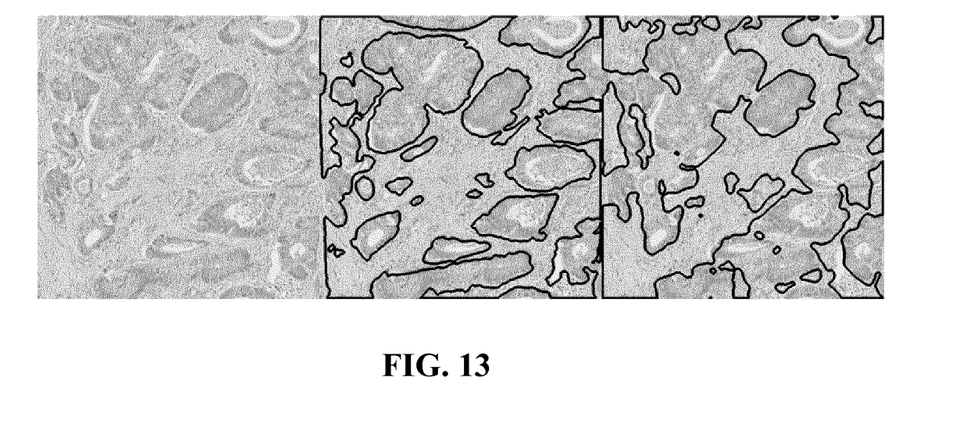
FIG. 13 shows the results obtained using an unseen image as the input image.

FIG. 13 shows the results for one such unseen example. Again, the input image is on the left, the desired mask image is in the centre, and the actual output of the algorithm is on the right. In this case, the input image was not part of the training dataset and so the neural network has no knowledge of the mask image in the centre. Nevertheless, it can be seen that the output of the neural network, shown overlaid on the image on the right, closely matches the desired mask. This confirms the ability of the method to generalise.

Figure 14A:
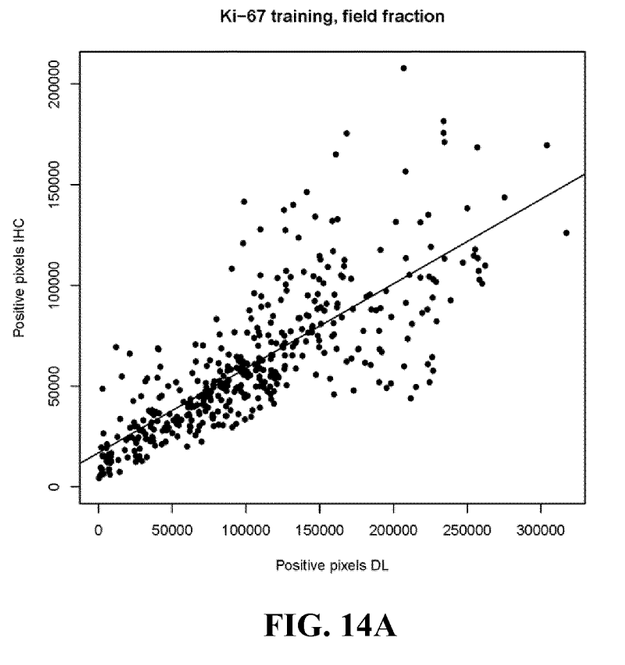
FIG. 14 is a scatter diagram showing results obtained using an image analysis method according to another embodiment of the second aspect of the invention.
Figure 14B:
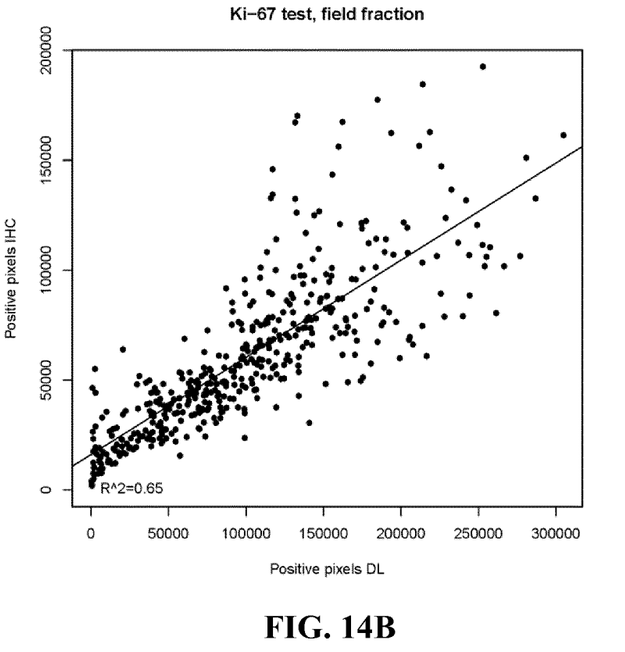

FIGS. 14A and 14B illustrate, on scatter plots, the results obtained for another embodiment of the present invention. In this case, the IHC marker is Ki67. Each data point plotted on the graph represents one patient. The variable plotted on the horizontal axis is the number of pixels in the mask detected by the method of the present invention. On the vertical axis is the number of pixels obtained with the conventional method of staining with Ki67. The plots show a strong correlation between the number of pixels detected according to the present invention and the number of pixels detected using the standard approach. A perfect result would involve all of the data points lining up in a straight line. Note that the slope of the line is not critical and is influenced by the threshold that is applied to generate each binary mask. The absolute number of pixels marked in the masks will depend on this threshold. But what is important is the relative correlation, independent of the precise thresholds chosen. FIG. 14A shows the results obtained on a training dataset; FIG. 14B shows the results obtained on a test dataset.

In general, the first marker, the second marker, or both, may comprise at least one IHC marker. A (non-exhaustive) list of relevant IHC markers in this context is as follows: Plk3, AR*, Klk4, PSA, Flotillin1, Flotillin2, PSMA, b-catenin, PCA3, PTEN*, Stamp1, Stamp2, sxBP1, B7H3, Adrb2, Vh1, Nkx1, PTEN*, Mx11, Foxo1A, Cdh1/E-cad, p53, Atbf1, Mcm7, EZH2, TcEB1, Eif353, c-myc, AR*, ERG, TMPRSS2, Mad1, Mad2, Bub1, Bubr1, Bub3, Cenp-E, Cyclin B, Securin, APC, AuroraB, Clasp1, Eb1, Eb1 (MAPRE2), FoxM1, Kif2FC (MCAK), Prpf4b, RANBP1, Rb1, SGOL1, SGOL2, AuroraA, CENPH, Axin 2, KIF11, ID1, MDM2, Plk1, Ki67, Gata2, Foxa1, CK5/14, CK8, CK18, CD44, p63, Bcl2, Cnx43, PKM2, ER, PR, HER2, PD-L1. The individual benefits and uses of each of these as markers will be familiar to those skilled in the art and need not be discussed in detail here.

While the invention has been illustrated and described in detail in the drawings and foregoing description, such illustration and description are to be considered illustrative or exemplary and not restrictive; the invention is not limited to the disclosed embodiments.

In some embodiments, the method of training the machine-learning algorithm may be implemented in an iterative fashion. The computer 100 may obtain a single first colour microscopic image and a single corresponding second colour microscopic image at a time. The computer may process this pair of images and may then check whether a sufficient number of images has been obtained to train the machine-learning algorithm. If not, the computer may repeat the process for a further pair of images. This procedure is repeated until the machine-learning algorithm is fully trained, at which point the iterations stop.

Furthermore, within each pair of images, individual tiles may be processed in an iterative fashion. That is, the computer may obtain a single tile from the first colour microscopic image and a corresponding single tile from the second colour microscopic image. The computer may process this pair of tiles and may then check if a sufficient number of tiles has been processed (or if all tiles of the present image-pair have been processed). If not, the computer may repeat the process for the next pair of tiles. This is repeated until a sufficient number of tiles has been processed or all tiles of the present image-pair of been processed.

Iterative implementations like these may lend themselves to a pipelined implementation of the training method. For example, the virtual microscope may begin scanning the next microscopic image while a previous microscopic image is being processed by the computer.

Of course, those skilled in the art will appreciate that controlling a virtual microscope to scan slides is not the only way for the computer 100 to obtain colour microscopic images. Libraries of suitable images may already be available from other sources. However, it is noted that training methods according to embodiments of the present invention require the existence of two corresponding sets of slide-images—one set in which the specimens are stained with a first marker and a second set in which the specimens are stained with a second marker.

The invention has been described by using the examples of H&E as the first marker and Vimentin as the second marker, and indeed this is one particularly advantageous use-case. However, other IHC markers may be used as the second marker. Examples include but are not limited to PD-L1, which can be used to detect T cell infiltrate; and Ki67, which can be used to detect cell proliferation.

In the examples described, the markers comprised colourants visible under a light microscope. However, the same principles are equally applicable to other markers such as fluorescent dyes.

Correspondingly, in the examples described above, the first and second microscopic images were colour microscopic images consisting of three colour channels. In other embodiments, such as those using fluorescent dyes, either or both of the microscopic images may have fewer than three colour channels. In particular, the microscopic images may be grayscale images, consisting of a single channel, or they may be two-channel images.

Although the steps of the training method were described above in a particular order with reference to FIG. 2, in general the steps need not be carried out in this order. For example, the steps of determining the geometric transformation and aligning the images may be performed before or after the step of obtaining the mask. In some embodiments, the first and second microscopic images may be aligned at the large-scale (step 232) and at the small-scale (step 272) before finally generating the mask image from the aligned tiles of the second microscopic image.

In the embodiments described above, the transformation mapping between the first microscopic image and the second microscopic image was a geometric transformation. However, this is not essential. In some embodiments, one or more non-geometric transformations may be used in place of or in addition to a geometric transformation. Such non-geometric transformations may be used to linearly or nonlinearly morph or warp one microscopic image to align it with another microscopic image.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A computer-implemented method of training a machine-learning algorithm to perform histopathological image analysis, the method comprising:
   obtaining (210), by the computer, a plurality of first microscopic images of first histological specimens that have been stained with a first marker;
   obtaining (212), by the computer, a respective plurality of second microscopic images of second histological specimens that have been stained with a second marker, different from the first marker, each one of the second histological specimens corresponding to a respective one of the first histological specimens;
   obtaining (220), by the computer, a respective plurality of mask images generated for the second microscopic images, each mask image identifying a histological feature of interest highlighted in the respective second microscopic image by the second marker;
   for each first microscopic image and the respective second microscopic image and mask image:
      obtaining (230, 270), by the computer, a transformation that maps between the first microscopic image and the second microscopic image, and
      aligning (232, 272), by the computer, the first microscopic image and the mask image, using the transformation; and
   training (240), by the computer, the machine-learning algorithm with the plurality of aligned first microscopic images and mask images,
   thereby training the machine-learning algorithm to predict, from another first microscopic image of another histological specimen stained with the first marker, a histological feature of interest that would be highlighted in that specimen by the second marker.

2. The method of claim 1, further comprising obtaining (250), by the computer, a region of interest in each of the first microscopic images,
   the method comprising training the machine-learning algorithm with said regions of interest and excluding from the training any regions other than said regions of interest.

3. The method of claim 1, further comprising dividing (262, 268), by the computer, each of the aligned first microscopic images and mask images into first tiles and mask tiles, respectively,
   the method comprising training (240) the machine-learning algorithm (245) with said first tiles and said mask tiles.

4. The method of claim 1, wherein obtaining the respective plurality of mask images comprises generating (220), by the computer, each mask image from the respective second microscopic image.

5. The method of claim 1, wherein one or both of the following steps is performed first at a coarse scale or resolution and subsequently performed at a fine scale or resolution:
   (a) obtaining (230, 270) the transformation; and
   (b) aligning (232, 272) the first microscopic image and the mask image.

6. The method of claim 1, wherein obtaining (230, 270) the transformation comprises extracting features of interest from the first microscopic image and the second microscopic image and establishing a mapping between the features of interest.

7. The method of claim 1, wherein the first marker comprises haemotoxylin and eosin.

8. The method of claim 1, wherein the second marker comprises an immunohistochemical marker.

9. The method of claim 1, wherein the first marker comprises a first immunohistochemical marker and the second marker comprises a second immunohistochemical marker.

10. The method of claim 1, wherein the second marker comprises a fluorescence marker.

11. The method of claim 1, wherein the machine-learning algorithm comprises a neural network.

12. The method of claim 1, further comprising training the machine-learning algorithm to predict, from a first microscopic image of a histological specimen stained with the first marker, a further histological feature of interest that would be highlighted in that specimen by a third marker, different from the first and second markers.

13. A computer-implemented method for histopathological image analysis, using a machine-learning algorithm trained according to the method of claim 1, the method comprising:
   obtaining (210a), by the computer, a first microscopic image of a histological specimen that has been stained with the first marker;
   providing, by the computer, the trained machine-learning algorithm (245);
   processing (242), by the computer, the first microscopic image using the machine-learning algorithm, to analyse the first microscopic image and generate a mask image (244),
   whereby the mask image identifies a histological feature of interest detectable using the second marker.

14. The method of claim 13, wherein the machine-learning algorithm has been trained to predict, from the first microscopic image, a further histological feature of interest detectable using a third marker,
   wherein, in processing the first microscopic image, the computer generates a further mask image identifying the further histological feature of interest.

15. The method of claim 13, further comprising conducting, by the computer, automated analysis of the mask image and/or the further mask image.

16. The method of claim 13, wherein the first marker comprises haemotoxylin and eosin.

17. The method of claim 13, wherein the second marker comprises an immunohistochemical marker.

18. The method of claim 13, wherein the first marker comprises a first immunohistochemical marker and the second marker comprises a second immunohistochemical marker.

19. The method of claim 13, wherein the second marker comprises a fluorescence marker.

20. A non-transitory computer-readable medium having embodied thereon a computer program comprising computer program code that when executed causes the computer to:
   obtain (210), by the computer, a plurality of first microscopic images of first histological specimens that have been stained with a first marker;

obtain (212), by the computer, a respective plurality of second microscopic images of second histological specimens that have been stained with a second marker, different from the first marker, each one of the second histological specimens corresponding to a respective one of the first histological specimens;

obtain (220), by the computer, a respective plurality of mask images generated for the second microscopic images, each mask image identifying a histological feature of interest highlighted in the respective second microscopic image by the second marker;

for each first microscopic image and the respective second microscopic image and mask image:
   obtain (230, 270), by the computer, a transformation that maps between the first microscopic image and the second microscopic image, and
   align (232, 272), by the computer, the first microscopic image and the mask image, using the transformation; and train (240), by the computer, the machine-learning algorithm with the plurality of aligned first microscopic images and mask images, and thereby train the machine-learning algorithm to predict, from another first microscopic image of another histological specimen stained with the first marker, a histological feature of interest that would be highlighted in that specimen by the second marker.

\* \* \* \* \*